United States Patent [19]

Hooven

[11] Patent Number: 4,681,559
[45] Date of Patent: Jul. 21, 1987

[54] PLURAL VALVE THREE STAGE PRESSURE RELIEF SYSTEM

[75] Inventor: Michael D. Hooven, Miami, Fla.

[73] Assignee: Cordis Corporation, Miami, Fla.

[21] Appl. No.: 812,781

[22] Filed: Dec. 23, 1985

[51] Int. Cl.⁴ .......................................... A61M 27/00
[52] U.S. Cl. .................................... 604/9; 137/504;
137/512.1; 604/247
[58] Field of Search ...................... 604/8–10,
604/247; 137/504, 512.1, 539

[56] References Cited

U.S. PATENT DOCUMENTS

| | | | |
|---|---|---|---|
| 28,722 | 6/1860 | Whitacker . | |
| 79,436 | 6/1968 | Bechtel . | |
| 1,139,455 | 5/1915 | Gase . | |
| 1,159,214 | 11/1915 | Gueux . | |
| 1,199,152 | 9/1916 | Bruce . | |
| 1,468,434 | 9/1923 | Zander . | |
| 2,207,382 | 7/1940 | McNamara | 277/21 |
| 2,290,151 | 7/1942 | McCollum | 237/12.3 |
| 2,969,066 | 1/1961 | Holter et al. | 128/350 |
| 3,109,429 | 11/1963 | Schwartz | 128/350 |
| 3,233,610 | 2/1966 | Wade | 128/350 |
| 3,270,771 | 9/1966 | Morgan | 137/525.3 |
| 3,288,142 | 11/1966 | Hakim | 238/350 |
| 3,308,719 | 3/1967 | Snider | 123/119 |
| 3,492,996 | 2/1970 | Fountain | 128/350 |
| 3,566,875 | 3/1971 | Stoehr | 128/350 |
| 3,601,128 | 8/1971 | Hakim | 128/350 |
| 3,654,932 | 4/1972 | Newkirk et al. | 128/350 V |
| 3,674,050 | 7/1972 | Kuffer et al. | 137/536 |
| 3,683,929 | 8/1972 | Holter | 128/350 V |
| 3,756,243 | 9/1973 | Schulte | 128/350 V |
| 3,768,508 | 10/1973 | Schulte | 137/522 |
| 3,769,982 | 11/1973 | Schulte | 128/350 |
| 3,782,410 | 1/1974 | Steuby | 137/496 |
| 3,804,113 | 4/1974 | Garcea | 137/496 |
| 3,827,439 | 8/1974 | Schulte et al. | 128/350 |
| 3,886,948 | 6/1975 | Hakim et al. | 128/350 V |
| 3,889,687 | 6/1975 | Harris | 128/350 V |
| 3,901,245 | 8/1975 | Spitz et al. | 128/350 V |
| 3,924,635 | 12/1975 | Hakim | 128/350 V |
| 3,970,105 | 7/1976 | Pelton et al. | 137/498 |
| 3,985,140 | 10/1976 | Harris | 128/350 V |
| 3,991,768 | 11/1976 | Portnoy | 128/350 |
| 3,999,553 | 12/1976 | Spitz | 128/350 |
| 4,103,689 | 8/1978 | Leighton | 128/350 V |
| 4,106,510 | 8/1978 | Hakim et al. | 128/350 V |
| 4,156,422 | 5/1979 | Hildebrandt et al. | 128/748 |
| 4,167,952 | 9/1979 | Reiniecke | 137/493 |
| 4,215,695 | 8/1980 | Spitz et al. | 128/350 |
| 4,246,930 | 1/1981 | Bishop | 137/493.9 |
| 4,261,341 | 4/1981 | Hakim et al. | 604/9 |
| 4,332,255 | 6/1982 | Hakim et al. | 128/350 |
| 4,340,038 | 7/1982 | McKean | 128/1.3 |
| 4,437,493 | 3/1984 | Okuda et al. | 138/45 |
| 4,443,214 | 4/1984 | Marion | 604/9 |
| 4,452,423 | 6/1984 | Bevlavi | 251/65 |

FOREIGN PATENT DOCUMENTS

| | | | |
|---|---|---|---|
| 702425 | 2/1941 | Fed. Rep. of Germany | 137/539 |
| 68509 | 8/1951 | Netherlands . | |

*Primary Examiner*—Dalton L. Truluck
*Attorney, Agent, or Firm*—Lockwood, Alex, FitzGibbon & Cummings

[57] ABSTRACT

An implantable valve for allowing the passage of cerebrospinal fluid (CSF) form a ventricle of the brain to a suitable drainage location in the body includes a plurality of fluid flow pressure differential responsive valves arranged in parallel relationship and having common inlet and outlet means, a portion of said inlet and outlet means imparting fluid flow restriction to the system in conjunction with the operation of at least one of said valves, the system being in pressure communication with the drainage location of the body and the ventricular spaces of the brain. When the pressure differential is relatively small, the system operates in a constant pressure mode to maintain a first predetermined pressure differential across the system. In response to a sudden increase in differential pressure, the system operates in a constant flow mode to maintain a desired relatively constant CSF flow rate through the system. Above a predetermined pressure differential, the system operates in a constant pressure mode to maintain a second predetermined maximum pressure differential across the system.

19 Claims, 5 Drawing Figures

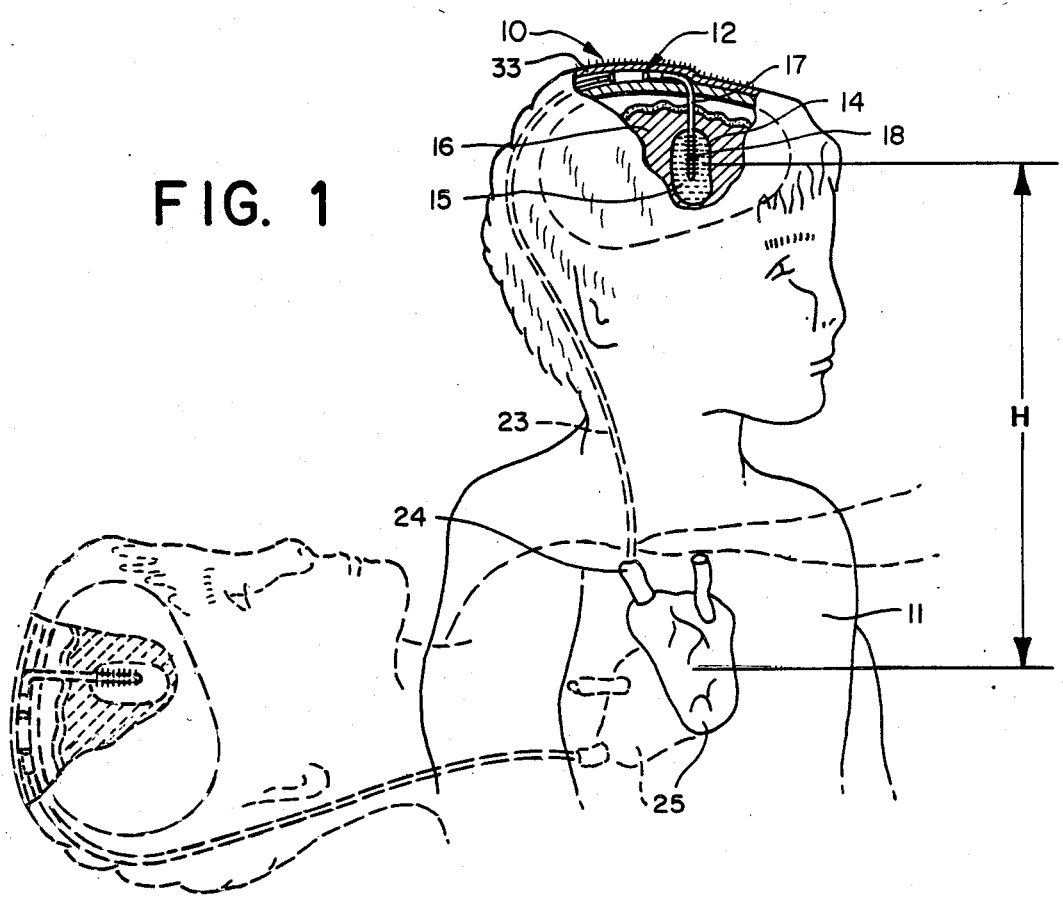
FIG. 1
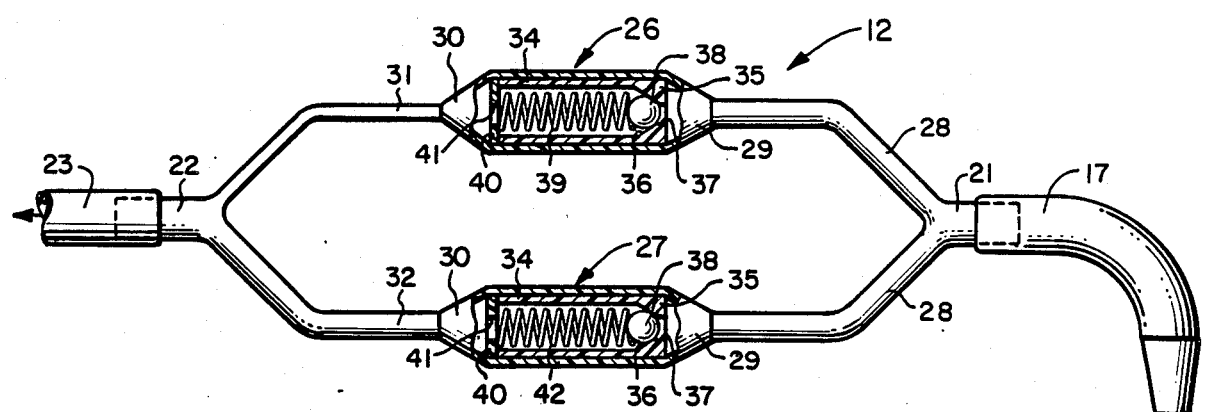
FIG. 2
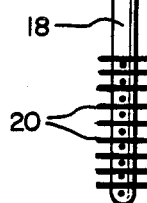

PLURAL VALVE THREE STAGE PRESSURE RELIEF SYSTEM

BACKGROUND OF THE INVENTION

The present invention relates to an intracranial pressure relief valve system and, more particularly, to a plural valve assembly for use in a three stage system which provides either constant pressure or constant flow characteristics in accordance with a fluid pressure differential applied across the system.

Hydrocephalus is a condition in which the body, for any one of a variety of reasons, is unable to relieve itself of excess cerebrospinal fluid (CSF) collected in the ventricles of the brain. The excessive collection of CSF in the ventricles results in an abnormal increase in both epidural and intradural pressures. This in turn may cause a number of adverse physiological effects including compression of brain tissue, impairment of blood flow in the brain tissue and impairment of the brain's normal metabolism.

Treatment of a hydrocephalic condition frequently involves relieving the abnormally high intracranial pressure. Accordingly, a variety of CSF pressure regulator valves and methods of controlling CSF pressure have been developed which include various check valves, servo valves or combinations thereof. Generally, such valves serve to divert CSF from the ventricles of the brain through a discharge line to some suitable drainage location in the body, such as the venous system or the peritoneal cavity. Check valves operate by opening when the difference between CSF pressure in the inlet line and pressure in the discharge line exceeds a predetermined value.

The use of a simple check valve, and nothing more, in the treatment of hydrocephalus is potentially disadvantageous since it is possible for such a valve to open in response to a sudden, but nevertheless perfectly normal, increase in differential pressure between CSF in the ventricular spaces and fluid at the selected discharge location of the body, resulting in abnormal and potentially dangerous hyperdrainage of the ventricular spaces. For example, when a patient stands after lying in a recumbent position, the resulting increased vertical height of the fluid column existing between the head and the selected drainage location may result in such an increase in differential pressure. Accordingly, valves, such as that described in the copending application of the present inventor, Serial No. 672,868, filed Nov. 19, 1984, have been developed which serve to prevent undesired hyperdrainage by limiting the flow rate of fluid through the valve when a sudden increase in differential pressure occurs.

In this valve, a diaphragm, movable in response to the pressure differential between ventricular CSF pressure and pressure of fluid at the drainage location of the body, was mechanically coupled to a valve seat having a fluid metering orifice extending therethrough. The orifice allowed passage of CSF from the ventricular spaces to the selected drainage location. Motion of the diaphragm in response to changes in the differential pressure caused the valve seat to be moved from a first position, in which the valve seat contacted a suitably located sphere to block and thereby prevent the passage of fluid through the orifice, to a second position, in which a generally cylindrical fluid flow to a second position, in which a generally cylindrical fluid flow restrictor partially occluded the orifice, thereby limiting fluid flow therethrough. By controlling the position of the sphere, the valve seat and the restrictor, it was possible to construct a valve having flow characteristics which avoided hyperdrainage with sudden changes in differential pressure.

As fluid flow resulting systems of the type under consideration are miniaturized, considerable manufacturing costs are incurred if the system includes valve components of rather complex configuration. This problem is further accentuated in a system involving the use of a substantial number of valve parts thereby increasing manufacturing costs.

The present invention is directed to an improved system in which more than one simple form of check valve, or equivalent, is utilized in a branched fluid flow circuit in which the valves merely respond to pressure differential differences while the circuit itself supplies fluid flow restriction in order to obtain the many advantages attendant to three stage pressure relief system operation.

In view of the foregoing, it is general object of the present invention to provide a new and improved pressure regulator valve for relieving intracranial pressure caused by the presence of excess CSF in the ventricles of the brain.

It is a more specific object of the present invention to provide a pressure regulator valve which includes components which may be readily and economically manufactured.

It is a still more specific object of the present invention to provide a pressure regulator valve in which critically dimensioned components are of a readily manufactured configuration.

SUMMARY OF THE INVENTION

The invention is directed to a plural valve, three stage pressure relief system for controlling the passage of body fluids from one location in the body to another location. The valve includes at least a pair of interior chambers which include valve means therein and which are in communication with port means for establishing fluid communication with the aforesaid locations. The valving means operate in response to selected predetermined pressure differentials to control fluid flow, and the port means further influence fluid flow by restricting the same under selected conditions. Accordingly, the system operates to provide a first condition in which fluid flow is prevented between the locations, a second condition in which fluid flow is sufficient to maintain a first substantially constant predetermined pressure in the one location, a third condition in which fluid flow is of a substantially constant rate between the locations, and a fourth condition in which fluid flow is sufficient to maintain a second substantially constant predetermined pressure in the one location.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a perspective view, partially in section, of a CSF pressure regulator system employing a three stage pressure regulator valve constructed in accordance with the invention, showing such a system implanted with a patient.

FIG. 2 is a plan view, partially in section, of the pressure regulator system and valve components thereof.

DESCRIPTION OF THE PREFERRED EMBODIMENT

Figure 3:
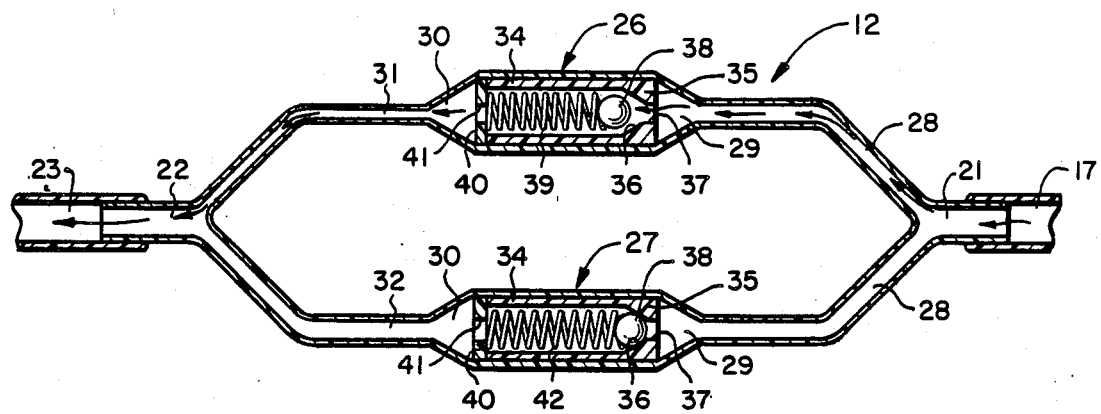
FIG. 3 is a cross-sectional view of the system illustrating certain aspects of operation thereof.

Referring to the drawings, and particularly to FIGS. 1 an 2, a CSF pressure relief system 10 for maintaining a desired predetermined intracranial pressure in a patient 11 is illustrated. The system shown includes a three stage pressure relief valve system 12 constructed in accordance with the present invention for maintaining the desired intracranial pressure.

Cerebrospinal fluid (CSF) 14 is drained from a ventricle 15 of the brain 16 by means of a ventricular catheter 17. Preferably, the catheter is radio-opaque in order to facilitate its accurate placement within the brain. The distal end 18 of the catheter may be provided with a plurality of apertures 20 (FIG. 2) for allowing the passage of CSF therethrough and is positioned in a suitable brain ventricle as illustrated. The other end of the catheter is coupled to the inlet port 21 of the valve system to establish fluid communication between the system and the ventricle. The outlet port 22 of the valve system is attached to one end of a drain catheter 23, the opposite end of which discharges into an appropriate location in the patient's body. Although the drain catheter is shown threaded through an appropriate vein 24 to terminate within the right atrium of the heart 25, a different drainage location, such as, for example, the peritoneal cavity, could be selected instead. When open, pressure relief valve system 12 allows passage of CSF from the brain ventricle to the selected discharge location to relieve excessive intracranial pressure caused by excessive accumulation of CSF.

While an increased differential pressure may result from the excessive accumulation of CSF in the brain ventricle, such an increase might also be a perfectly normal response to ordinary physical activity of the patient. For example, when a patient stands after lying for some time in a recumbent position, as illustrated in phantom in FIG. 1, the differential pressure will suddenly increase by reason of the sudden increase in vertical height H in the fluid column existing between the distal end of the ventricular catheter 17 and the drainage location. If a relief valve of the system were to open and permit unrestrained fluid flow in response to this pressure increase, hyperdrainage of the ventricle and a brain hematoma, are possible results. Accordingly, the valve system includes means for preventing such an unrestricted fluid flow to the drainage location in the event of a sudden increase in the differential pressure.

The internal construction of the three stage valve system may best be understood by reference to the FIG. 2. In the embodiment illustrated, the valve system includes a pair of tubular fluid flow chambers 26 and 27 which are arranged in parallel flow relationship and which contain therein valving means to control fluid flow through the system. The inlet port 21 is bifurcated to provide a pair of tube-like inlet passages 28 extending into communication with the chambers 26 and 27. The tubes or passages 28 are in fluid communication with fluid flow end members 29 which form a part of the tube-like chambers 26 and 27 at the inlet ends thereof. End members 30 of similar construction define outlet areas of the chambers 26 and 27 and are, in turn, suitably connected to tube-like passages 31 and 32 which integrally converge with the outlet port 22. The lumen of the tube or passageway 31 is of smaller or restricted diameter as compared to that of the tubes 28 and 32, the lumen of the latter tubes being of equal diameter in the preferred embodiment. The tube 31 constitutes a restrictor means to control the flow of fluid in the system as will be described.

The tubes, end members and chambers described may be formed from any suitable biocompatible material, such as thermoplastic polymers of polyethersulfone or polycarbonates. If desired, that portion of the system described may be incorporated in an outer housing (not shown) formed of silicone rubber, or a similar material, to assist in implanting the system over the cranium 33 (FIG. 1). The dimension of the various parts described are selected so as to be compatible with subcutaneous implantation of the valve over the cranium 33.

Valve assemblies of similar configuration are mounted in the chambers 26 and 27. Referring first to the valve assembly of the chamber 26, this assembly includes an assembly housing 34 of tubular configuration having at the input end thereof a valve seat 35 presenting interiorly thereof a frusto-conical surface 36 which at the outer terminus thereof defines a fluid flow orifice 37. The valve seat 35 receives against the frusto-conical surface 36 thereof a ball or check valve member 38 which is urged against the seat by a coil spring 39 extending longitudinally of the housing and coaxially relative to the ball and valve seat. The opposite end of the spring 39 is retained within the housing by an annular end plate 40, or spring retainer seat, which is provided with a fluid flow opening 41 centrally thereof to permit fluid to exit from the chamber 26 into the smaller diameter tube or restrictor 31.

The tubular chamber 27 includes a similar valve assembly having the various parts just described in connection with the chamber 26, and accordingly, like reference numerals are used to identify similar parts. The only exception is that the valve assembly in the chamber 27 utilizes a coil spring 42 which is of different calibration as compared to the coil spring 39 as will be described. The valve assembly within the chamber 27 controls fluid flow from the inlet tube 28 through the normal size discharge tube 32 to the outlet 22. The balls or spheres 38 are highly polished and may be formed of synthetic sapphire with the valve housings 34 and springs 39 and 42 being formed from stainless steel.

Basically, the pressure relief valve system 12 normally operates to maintain a predetermined differential pressure $P_1$ between fluids in the brain ventricle and at the selected discharge location of the body. The system accomplishes this by adjusting the fluid flow rate Q so that the pressure $P_1$ is maintained. This operation of the system is shown in region I of FIG. 5. FIG. 3 illustrates the valve assembly in chamber 26 operating in region I when the fluid differential pressure is sufficient to displace the sphere 38 from the valve seat 35 against the action of the spring 39, thereby permitting fluid flow. Thus, in the mode of operation, the valve assembly of chamber 26 is functioning as a conventional low pressure shunt. During this stage of operation the valve assembly in chamber 27 remains closed by reason of the spring 42 thereof being calibrated to remain non-responsive to relatively low differential pressures on the order of $P_1$.

Figure 5:
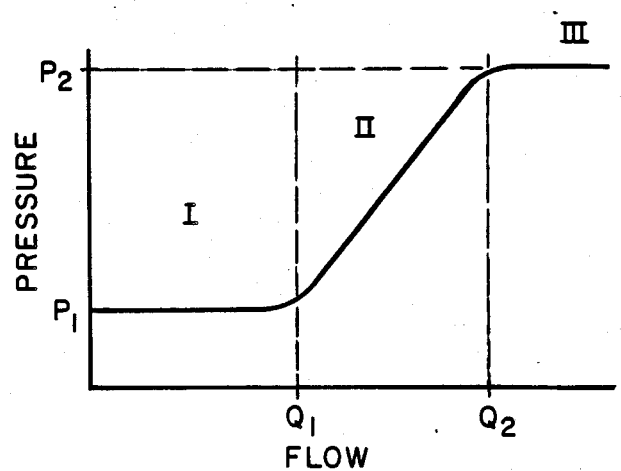
FIG. 5 is a graphical depiction of certain pressure and flow characteristics of the three stage pressure regulator valve system useful in understanding the operation thereof.

Referring in particular to FIG. 5, when differential pressure rapidly increases, such as when the patient stands, a flow rate greater than pre-selected rate $Q_1$ is necessary to maintain pressure $P_1$. However, such flow rate may create the risk of undesirable hyperdrainage of the brain ventricle. Accordingly, when a rapid increase in differential pressure occurs, the valve automatically serves to maintain a relatively constant desired rate of fluid flow despite changes in differential pressure, as depicted in region II of FIG. 5. In a practical valve system the flow rate will not be entirely independent of the applied differential pressure but rather will increase from a lower flow rate $Q_1$ to a higher flow rate $Q_2$ as differential pressure increases between first pressure $P_1$ and a second pressure $P_2$, as indicated by the solid line in FIG. 5. Flow rates $Q_1$ and $Q_2$ are sufficiently low so that during a temporary rapid increase in differential pressure, pressure will return to normal before a quantity of CSF sufficient to cause adverse side effects may flow through the system. In a typical system, $Q_1$ and $Q_2$ might be 0.4 ml./min. and 0.8 ml./min., respectively.

While FIG. 3 illustrates the operation of the present system during the second mode of operation wherein the valve assembly in chamber 26 acts primarily as a constant pressure device with the pressure differential $P_1$ being maintained between the CSF in the brain ventricle and the CSF in the discharge location, this illustration can also be utilized in understanding the third mode of operation of the system wherein a desired rate of fluid flow is maintained despite changes in differential pressure. The valve assembly of the chamber 26 is open thereby not offering any resistance to fluid flow through the chamber 26. When a sudden increase in differential pressure occurs, such as to cause operation of the system within region II of FIG. 5, the discharge tube 31 by reason of its smaller diameter (smaller lumen) and, therefore, its limited capacity to accommodate fluid flow volume, offsets any higher flow rate ordinarily resulting from increased pressure. This provides a relatively uniform rate of fluid flow discharged from chamber 26 into outlet 22. Thus, relatively high resistance to fluid flow is created at the discharge end of chamber 26 to limit the rate of fluid flow thereby preventing any undesirable rapid shunting of CSF which might result in possible brain damage.

To avoid the possibility of building extremely high ventricular CSF pressure, the valving system is constructed so that when differential pressure exceeds a predetermined pressure $P_2$, substantially higher than pressure $P_1$, the system operates to allow a fluid flow rate sufficient to maintain a differential pressure no higher than pressure $P_2$. This operation is depicted in region III of FIG. 5. When the system is operating in this region, further increases in differential pressure result in an increase in fluid flow through the system thereby stabilizing differential pressure.

Figure 4:
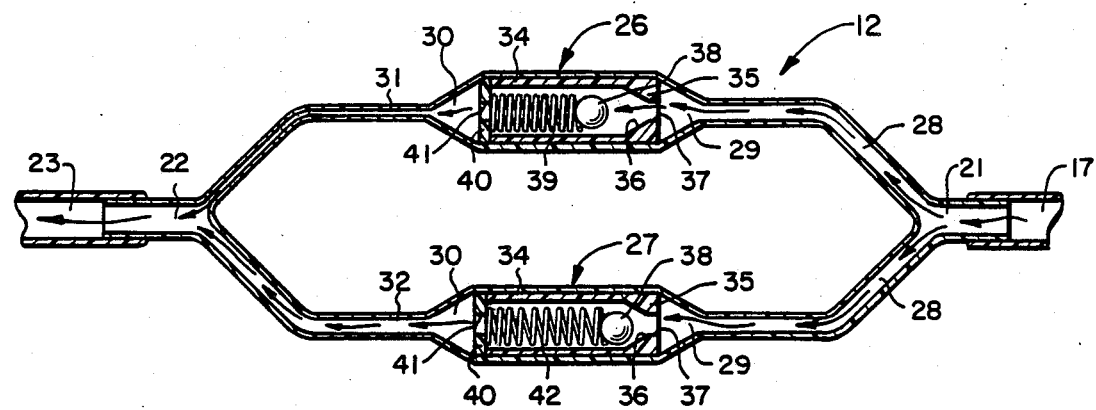
FIG. 4 is a view similar to FIG. 3 illustrating further aspects of the operation of the system.

FIG. 4 illustrates operation of the system in region III of FIG. 5. As can be seen, both valve assemblies of chambers 26 and 27 are now open and unresisting to fluid flow, except for the resistance offered by the smaller lumen of outlet tube 31 of chamber 26. Upon reaching a predetermined pressure differential build-up, the resistance of the spring 42 in chamber 27 is overcome and the sphere 38 is displaced from the valve seat 35 to permit fluid flow through the chamber 27. The inlet and outlet passages, or tubes 28 and 32, in communication with chamber 27 are unrestricted, or are of normal diameter (lumen), so as to accommodate a substantial increase in fluid flow. The valve assembly of chamber 26 remains open, and in this mode of operation the entire system is transferring fluid from the brain ventricle to the discharge location. Thus, the system operates essentially as a constant pressure device whereby differential pressure greater than the predetermined maximum pressure $P_2$ is prevented.

It can be appreciated that the combination of two conventional constant pressure valves in parallel within a system provided with a high resistance in series with the low pressure valve will provide three stage operation as well as additional advantages. While a well known type of check valve has been illustrated in the system, it will be understood that other forms of valve mechanisms may be used. Check valves of the type illustrated may be readily manufactured at lower cost not only because of the simplicity of such valves, but also because of the accumulated knowledge concerning the same. In this particular system, the on-off type of valve operation simplifies manufacturing requirements and attendant costs. The low pressure valve in chamber 26 may be provided with a closing pressure ranging from about 21 to 55 millimeters of water. The high pressure valve of chamber 27 may have an opening pressure in the range of about 350 to 165 millimeters of water. The lumen of the smaller diameter tubing 31 applying the constant flow rate characteristics to the system will be selected consistent with the calibration of the springs 39 and 42. While it is preferred that the flow restrictor tubing 31 to be located at the discharge end of the low pressure chamber, it can be utilized at the inlet end of such chamber with at least similar results.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. A valve for controlling the passage of body fluids from a first location in the body to a second location, comprising:

catheter means for removing a fluid from said first body location;

drain means for discharging said fluid to said second location;

first and second fluid passages in parallel fluid flow communication between said catheter means and said drain means;

said first fluid passage having a first valve means for regulating fluid flow through said first fluid passage, wherein said first valve means opens at a first predetermined pressure, said first fluid passage also having fluid flow restrictor means for resisting sudden increases in flow rate through said valve; and said second fluid passage having a second valve means for regulating fluid flow through said second fluid passage wherein said second valve means opens at a second predetermined pressure greater than said first predetermined pressure.

2. The valve of claim 1, wherein said first and second valve means are check valves.

3. The valve of claim 2, wherein each said check valve includes a valve seat, a ball valve member which engages said valve seat to seal said check valve and urging means for urging said ball member towards said valve seat.

4. The valve of claim 3, wherein said fluid flow restrictor means is a constricted portion of said first fluid passage.

5. The valve of claim 1, wherein said first and second fluid passages have a substantially circular cross section.

6. The valve of claim 3, wherein said first and second fluid passages have a substantially circular cross section.

7. An intracranial pressure regulator valve for controlling the transfer of cerebrospinal fluid from a first location within the body to a second location, said valve comprising:
- catheter means for removing a fluid from said first body location;
- drain means for discharging said fluid to said second location;
- a first fluid flow chamber, said first chamber having a first valve means for regulating fluid flow through said first chamber whereby said first valve means opens at a first predetermined pressure;
- fluid flow restrictor means associated with said first fluid flow chamber for resisting sudden increases in flow rate through said valve;
- a second fluid flow chamber, said second chamber having a second valve means for regulating fluid flow through said second chamber whereby said second valve means opens at a second predetermined pressure, said second predetermined pressure being greater than said first predetermined pressure;
- inlet conduit means for directing said fluid from said catheter means to said first and second chambers whereby said first and second chambers are arranged in parallel fluid flow relation; and outlet conduit means for directing said fluid from said first and second chambers to said drain means.

8. The regulator valve of claim 7 wherein said first and second valve means are check valves.

9. The regulator valve of claim 8, wherein each said check valve includes a valve seat, a ball valve member which engages said valve seat to seal said check valve and urging means for urging said ball member towards said valve seat.

10. The regulator valve of claim 7, wherein said fluid flow restrictor means is a constricted portion of said first fluid flow chamber.

11. The regulator valve of claim 22, wherein said first and second fluid flow chambers, said inlet conduit means and said outlet conduit means all have substantially circular cross sections.

12. The regulator valve of claim 10, wherein said first and second flow chambers, said inlet conduit means and said outlet means all have substantially circular cross sections.

13. An intracranial pressure regulator valve for controlling the transfer of cerebrospinal fluid from a first location within the body to a second location, said valve comprising:
- a catheter for removing a fluid from said first body location;
- drain means for discharging said fluid to said second location;
- a first fluid flow chamber, said first chamber having a first valve means therein for regulating fluid flow through said first chamber whereby said first valve means opens at a first predetermined pressure differential between said first and second locations, an inlet opening for introducing said fluid into said first chamber and a discharge opening for discharging said fluid from said first chamber;
- a second fluid flow chamber, said second chamber having a second valve means therein for regulating fluid flow through said second chamber whereby said second valve means opens at a second predetermined pressure differential between said first and second locations, said second predetermined pressure differential being greater than said first predetermined pressure differential, an inlet opening for introducing said fluid into said second chamber and a discharge opening for discharging said fluid from said second chamber;
- inlet conduit means for directing said fluid from said catheter means to said first and second flow chambers whereby said first and second chambers are arranged in parallel fluid flow relation;
- outlet conduit means for directing said fluid from said first and second chanbers to said drain means;
- fluid flow restrictor means associated with said first fluid flow chamber for resisting sudden increases in flow rate through said valve wherein said restrictor means and said first fluid flow chamber are arranged in series fluid flow relation; and
- whereby said regulator valve operates in a first condition in which fluid flow between said first and second locations is prevented, a second condition in which fluid flow through said regulator valve is sufficient to maintain a first substantially constant predetermined pressure differential between said first location and said second location, a third condition in which fluid flow is at a substantially constant rate through said regulator valve, and a fourth condition in which fluid flow through said regulator valve is sufficient to maintain a second substantially constant predetermined pressure differential between said first location and said second location, wherein said second substantially constant predetermined pressure differential is greater than said first substantially constant predetermined pressure differential.

14. The regulator valve of claim 13, wherein said first and second valve means are check valves.

15. The regulator valve of claim 14, wherein each said check valve includes a valve seat, a ball valve member which engages said valve seat to seal said check valve and urging means for urging said ball member towards said valve seat.

16. The regulator valve of claim 13, wherein said fluid flow restrictor means is a constricted portion of said outlet conduit means.

17. The regulator valve of claim 14, wherein said fluid flow restrictor means is a constricted portion of said inlet conduit means.

18. The regulator valve of claim 12, wherein said first and second fluid flow chambers, said inlet conduit means and said outlet conduit means all have substantially circular cross sections.

19. The regulator valve of claim 16, wherein said first and second flow chambers, said inlet conduit means and said outlet conduit means all have substantially circular cross sections.

* * * * *